(12) United States Patent
Miki et al.

(10) Patent No.: US 6,653,278 B1
(45) Date of Patent: Nov. 25, 2003

(54) SELENIUM-CONTAINING PRO-DRUGS FOR CANCER THERAPY

(75) Inventors: Kenji Miki, Tokyo (JP); Mingxu Xu, San Diego, CA (US); Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/568,902

(22) Filed: May 11, 2000

Related U.S. Application Data

(60) Provisional application No. 60/133,678, filed on May 11, 1999.

(51) Int. Cl.[7] .................. A01N 37/18; A01N 61/00; C07K 1/00; A61K 38/51
(52) U.S. Cl. ..................... 514/2; 514/1; 530/350; 424/94.5
(58) Field of Search ................. 514/1, 2; 530/350; 424/94.5

(56) References Cited

U.S. PATENT DOCUMENTS

| | | | |
|---|---|---|---|
| 4,512,977 A | 4/1985 | Lundy | 424/132 |
| 5,104,852 A | 4/1992 | Kralick et al. | 514/6 |
| 5,597,829 A | * 1/1997 | Hauhsheer et al. | 514/283 |
| 5,783,454 A | 7/1998 | Spallholz et al. | 436/525 |

FOREIGN PATENT DOCUMENTS

| WO | WO 94/11535 | 5/1994 |
|---|---|---|

OTHER PUBLICATIONS

Eck et al., Gene–Based Therapy, 1996, Goodman & Gilman's, Chapter 5, pp. 77–101.*
Andreadou et al., Synthesis of Novel Se–Substituted Selenocystein . . . , 1996, J. Med. Chem., vol. 39, pp. 2040–2046.*
Allen et al., Synthesis ansd utilization of theraprutic agents for the treatment of lysosomal storage diseases, Jul. 18, 1995, pp. 1–8.*
Dachs G. et al. (1997). *Oncology* 9(9):313–325.
El–Bauyoumy, K. et al. (1992). *Cancer Res* 52:2402–2407.
Ip et al. (1990). *Cancer Res* 50:1206–1211.
Kajander, E.O. et al. (1990). *Biochem J* 267:767–774.
Miki, K. et al. (2000). *Proc Natl Acad Sci USA* 41:670.
Niculescu–Duvaz, I. et al. (1998). *Bioconjugate Chemistry* 9(1):4–22.
Spallholz, J.E. (1994). *Free Radical Biology & Medicine* 17:45–64.
Stewart, M.J. et al. (1999). *Free Radical Biology & Medicine* 26:42–48.
Yan, Y. et al. (1993). *Biochem Pharmacol* 45:429–437.

* cited by examiner

*Primary Examiner*—Shin-Lin Chen
(74) *Attorney, Agent, or Firm*—Morrison Foerster LLP

(57) ABSTRACT

Methods for inhibiting the growth of tumor cells by combination treatment with a selenium-containing prodrug and an enzyme for which it is a substrate are described. The treatment also enhances the effect of anti-tumor agents.

6 Claims, 9 Drawing Sheets

SELENIUM-CONTAINING PRO-DRUGS FOR CANCER THERAPY

CROSS-REFERENCE TO RELATED APPLICATIONS

This application claims priority from Provisional Application 60/133,678 filed May 11, 1999. The contents of that application are incorporated herein by reference.

TECHNICAL FIELD

The invention relates to the use of the combination of a lyase with a selenium-containing lyase substrate to inhibit or destroy tumor cells in vitro and in vivo. More specifically, the invention concerns providing an enzyme capable of generating a toxic selenium form from a relatively nontoxic substrate in combination with said substrate. An illustrative combination is selenomethionine in combination with methioninase. The enzyme may be supplied directly or generated recombinantly in situ.

BACKGROUND ART

Selenium is an element essential for metabolism, but in the wrong form and in inappropriate amounts it is cytotoxic. This may be advantageous in the context of carcinostatic properties. Spallholz, J. E., in a review article published in *Free Radical Biology and Medicine* (1994) 17:45–64, proposed that the toxic selenium species is the metabolic selenide $RSe^-$ anion. The anion can participate in transthiolation reactions and generate superoxide, hydrogen peroxide and perhaps other cascading oxyradicals, according to this proposal. In a later paper from the same group, Stewart, M. J., et al., *Free Radical Biology and Medicine* (1999) 26:42–48, it is reported that catalytic selenite, selenocystine and selenocystamine induced apoptosis and were cytotoxic in keratinocytes, but selenomethionine was not cytotoxic and did not induce cellular apoptosis at the concentrations studied. Selenomethionine has also been shown to act as a cancer chemoprotectant by Ip, et al., *Cancer Res.* (1990) 50:1206–1211; El-Bayoumy, K., et al., *Cancer Res.* (1992) 52:2402–2407. Selenium compounds shown to inhibit carcinogenesis in rodents have been reported by Yan, Y., et aL, *Biochem. Pharmocol.* (1993) 45:429–437.

Apparently, diselenide forms of organic selenium compounds, such as selenocystine and selenocystamine can be converted to the toxic form $RSe^-$. However, mammalian cells do not readily convert the monoselenide forms to toxic moieties. Thus, selenomethionine, selenohomocysteine and seleriocysteine are relatively nontoxic and noricarcinostatic.

Selenodithiols have been used to inhibit proliferation of cancer cells as described in U.S. Pat. No. 5,104,852 and selenium compounds which would otherwise be toxic have been used therapeutically in small enough concentrations as described in U.S. Pat. No. 4,512,977.

It has now been found that a particularly effective protocol for treatment of tumors comprises using the nontoxic forms of selenium as prodrugs when the targeted cells are provided with a means to convert the pro-drugs to the toxic forms. The pro-drugs themselves can be cytotoxic if at sufficiently high levels. Kajander, E. O., et al., *Biochem. J* (1990) 267:767–774. However, these levels are several orders of magnitude higher than those required for cytotoxicity of compounds that can readily generate $RSe^-$ in cells.

DISCLOSURE OF THE INVENTION

The invention is directed to protocols and formulations for selectively killing cancer cells through the combination of an $RSe^-$ generating enzyme, such as methioninase and its selenium-containing substrate, e.g., selenomethionine. The method can be used in chemotherapy regimen to treat a variety of cancers. The selenium-containing prodrug and/or the methioninase can also be selectively targeted to a particular cancer cell type or to a tumor site. The methioninase can be administered as a nucleic acid comprising a nucleotide sequence which encodes the enzyme that is expressible by the cancer cells or by other target host cells. The methioninase and the selenium-containing prodrug can also be directly administered to the tumor site, where possible or desired. The protocols cause cell death or retard cell growth.

The selenium-containing prodrugs include selenomethionine and related compounds. The prodrug is cleaved by a lyase at the C-Se bond to result in the release of. the active selenide moiety. This moiety is thought to be a methylselonide or a related compound of the formula $RSe^-$ where R is hydrocarbyl or H.

The enzyme administered will be one which serves as a lyase for the selenium-containing prodrug. If the selenium-containing prodrug is selenomethionine, methioninase is an appropriate choice.

Methioninase can be recombinantly produced or purified from natural sources. For example see U.S. Pat. No. 5,690,929. An expression system or cassette for production of methioninase can be used in place of the enzyme or along with it if desired. The vector permits the selective expression of the enzyme, which would localize its presence at a selected or desired site. Further, the methioninase can be complexed with a targeting molecule, e.g. an antibody that recognizes cancer cells. See, e.g. U.S. Pat. No. 5,057,313. The selenium-containing prodrug can similarly be targeted.

Thus, in one aspect, the invention is directed to a method to inhibit tumor cell growth which method comprises contacting said tumor cells with a selenium-containing prodrug and with an enzyme that liberates a toxic form of selenium from said prodrug in amounts sufficient to inhibit said tumor cell growth. In a preferred embodiment, the enzyme is an $\alpha,\gamma$-lyase or an $\alpha,\beta$-lyase and the selenium-containing prodrug is a corresponding sulfur-containing amino acid or the corresponding amine. In one preferred embodiment, the lyase is supplied by generating it internally to the targeted tumor cells or in cells adjacent to them by providing a suitable: expression system to said cells or their neighbors.

MODES OF CARRYING OUT THE INVENTION

Figure 1:
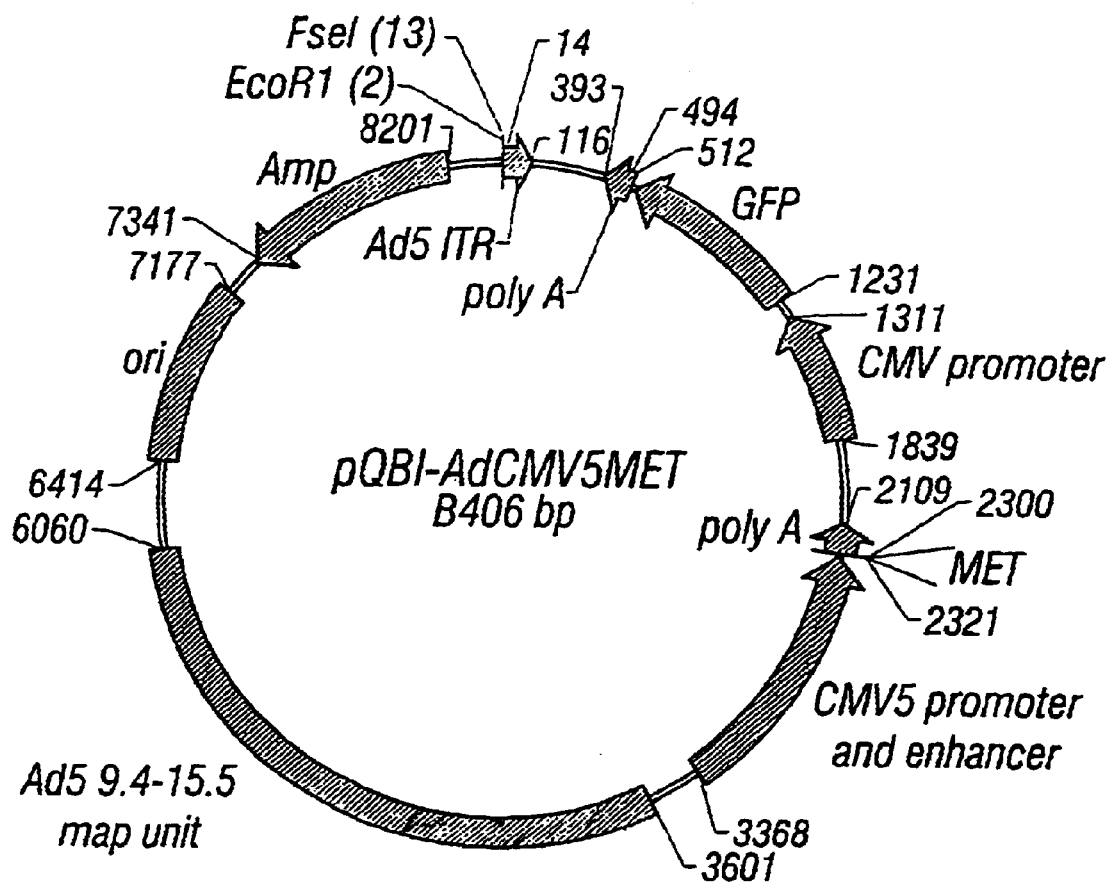
FIG. 1 shows a diagram of the vector used for production of methioninase in situ, pQBI-Ad CMV 5MET.

It is understood that the toxicity of a selenium-based compound is highly dependent on the nature of the compound. Certain selenium compounds which are able to generate selenium anions of the general formula RSe⁻ where R is H or a hydrocarbyl substituent are highly toxic. Forms of selenium which are known to be capable of generating this toxic moiety include the inorganic moiety selenite and organic diselenide compounds such as selenocystamine and selenocystine. However, other compounds, in particular the selenated forms of the sulfur-containing amino acids homocysteine, cysteine and methionine and their corresponding decarboxylated forms do not generate the, toxic form of selenium in mammalian cells.

However, there are a number of enzymes derivable from non-mammalian sources that are able to lyse these substrates and generate toxic forms of selenium. These enzymes include L-methionine γ-lyase from Aeromonas (Nakayama, T., et al., *Agric. Biol. Chem.* (1984) 48:2367–2369) which utilizes methionine, ethionine, homocysteine and acetyl L-homoserine as substrates; the methionine γ-lyase from *Pseudomonas putida* described by Nakayama, T., et al., *Analyt. Biochem.* (1984) 138:421–424, which has a similar substrate spectrum; and the L-methionine γ-lyase from Pseudomonas ovalis, Tanaka, H., et al., *Biochemistry* (1977) 16:100–106. A detailed description of these enzymes (EC 4.4.1.11) is found in an article by Esaki, N., et al., *Methods in Enzymology* (1987) 143:459–465. The anti-tumor activity of this enzyme itself has been described by Tanaka, H., et al., *J. Applied Biochem.* (1980) 2:439–444 and the gene encoding the *P. putida* enzyme as well as other corresponding enzymes have been cloned. See Inoue, H., etal., *J. Biochem.* (1995) 117:1120–1125. See also PCT publication WO 99/05311 and U.S. Pat. No. 5,861,154 and 5,863,788. The ability of the methionine γ-lyase from *P. putida* to catalyze the replacement of the methylthio moiety in methionine to obtain the corresponding selenium-containing form has also been disclosed by Esaki, N., et al., *Biochemistry* (1979) 18:407–411. It appears, based on the results described in this paper, that amino acids other than methionine wherein,the methyl group is replaced by an alkyl substituent or even a phenyl or benzyl substituent are suitable substrates for this enzyme.

Thus, the selenium-containing prodrug may be any selenium-containing compound that can behave as a substrate for an appropriate enzyme to generate the toxic form of selenium, believed to be RSe⁻ wherein R is H or hydrocarbyl, typically alkyl, phenyl or benzyl. The nature of this group is dependent only on the specificity of the enzyme.

The enzyme is typically a lyase of the type described above. However, any enzyme which dissociates the selenium-containing prodrug to generate the toxic selenium form is workable in the method of the invention. Such enzymes are referred to herein as "selenium prodrug lyase (s)."

The selenium prodrug lyase may be supplied as a protein or may be generated intracellularly or in situ by supplying an expression system for the enzyme. If the enzyme per se is administered, methods for administering such proteins are generally known in the art. For example, methods to administer methioninase in particular, in the context of chemotherapy are set forth in U.S. Pat. No. 5,690,929, the contents of which are incorporated herein by reference. Proteins in general can be administered by injection, typically intravenous injection or by transmembrane administration, for example, intranasally or using suppositories. Other modes of administration are also possible, including oral administration provided adequate protection from hydrolysis is included in the formulation. Such methods are generally known in the art as described in *Remington's Pharmaceutical Sciences*, latest edition, Mack Publishing Company, Easton Pa.

The protein may be administered per se or it may also include a targeting agent to direct the protein specifically to tumor cells. Such targeting agents may include, for example, antibodies or immunologically reactive fragments thereof, including single-chain antibodies, which are immunospecific for antigens associated with tumor cells or for antigens which appear on the organs in which the tumors reside, such as prostate-specific antigen in the case of prostate cancer. In addition, the targeting agents may include ligands for receptors that characterize the cells associated with the tumor. Coupling to such fargeting agents is also conventional and involves standard linking technologies, optionally utilizing commercially available linkers, such as those available from Pierce Chemical Company, Rockford Ill.

If the selenium prodrug lyase is to be generated intracellularly or in situ, a suitable nucleic acid molecule containing the nucleotide sequence encoding the enzyme is administered. Suitable modes of administration include injection, topical administration in formulations that include agents which enhance transmembrane or transdermal transit or any other appropriate and convenient method consistent with the situs of the tumor cells and the nature of the formulation, as will be understood by the ordinary practitioner. One particularly preferred mode of administration is local to the tumor—i.e., the nucleic acid molecule may be administered directly to the tumor tissue or to the site where the tumor resides. Because the formulations of the invention are able to provide not only a cytotoxic effect on the cells containing the prodrug and enzyme but also a bystander effect on neighboring cells, direct administration to the locus of the tumor is often satisfactory.

The nucleic acid molecule is typically a vector, most commonly a viral vector, although naked DNA can, in some instances, be used. The viral vectors may be retroviral vectors, which preferentially replicate in rapidly proliferating cells, thus conferring specificity for tumor cells on the vector, or may include adenoviral vectors or other conventional vector-based molecules. Specificity in this case may be conferred by localized administration and/or by placing the expression of the nucleotide sequence encoding the enzyme under control of a promoter which is operable selectively in tumor tissue. Table 1 below sets forth a list of tumor-associated viruses and oncogenes which comprise promoters specific for the tumors with which they are associated. Promoters associated with these genes and viruses may be used to direct expression selectively in the appropriate tumor.

TABLE 1

Oncogenes and tumor viruses

| Acronym | Virus | Species | Tumor origin | Comments |
|---|---|---|---|---|
| abl | Abelson leukemia | Mouse | Chronic myelogenous leukemia | TyrPK(src) |
| erbA | Erythroblastosis | Chicken | | Homology to human glucocorticoid receptor |
| erbB | Erythroblastosis | Chicken | | TryPK EGF/TGFc receptor |
| ets | E26 myeloblastosis | Chicken | | Nuclear |
| fes (fps)[a] | Snyder-Thellen sarcoma Gardner-Arnstein sarcoma | Cat | | TryPK(src) |
| fgr | Gardner-Rasheed sarcoma | Cat | | TyrPK(src) |
| fms | McDonough sarcoma | Cat | | TyrPK CSF-1 receptor |
| fps (fes)[a] | Fujinami sarcoma | Chicken | | TyrPK(src) |
| fos | FBJ osteosarcoma | Mouse | | Nuclear, TR |
| hst | NVT | Human | Stomach tumor | FGF homologue |
| intl | NVT | Mouse | MMTV-induced carcinoma | Nuclear, TR |
| int2 | NVT | Mouse | MMTV-induced carcinoma | FGF homologue |
| jun | ASV17 sarcoma | Chicken | | Nuclear, TR |
| hit | Hardy-Zuckerman 4 sarcoma | Cat | | TyrPK GFR L |
| B-lym | NVT | Chicken | Bursal lymphoma | |
| mas | NVT | Human | Epidermoid carcinoma | Potentiates response to angiotensin II |
| met | NVT | Mouse | Osteosarcoma | TyrPK GFR L |
| mil (raf)[b] | Mill Hill 2 acute leukemia | Chicken | | Ser/ThrPK |
| mos | Moloney sarcoma | Mouse | | Ser/ThrPK |
| myb | Myeloblastosis | Chicken | Leukemia | Nuclear, TR |
| myc | MC29 myelocytomatosis | Chicken | Lymphomas | Nuclear TR |
| N-myc | NVT | Human | Neuroblastomas | Nuclear |
| neu (ErbB2) | NVT | Rat | Neuroblastoma | TryPK GFR L |
| ral (mil)[b] | 3611 sarcoma | Mouse | | Ser/ThrPK |
| Ha-ras | Harvey murine sarcoma | Rat | Bladder, mammary and skin carcinomas | GTP-binding |
| Ki-ras | Kirsten murine sarcoma | Rat | Lung, colon carcinomas | GTP-binding |
| N-ras | NVT | Human | Neuroblastomas leukaemias | GTP-binding |
| rel | Reticuloendothe-liosis | Turkey | | |
| ros | UR2 | Chicken | | TyrPK GFR L |
| sis | Simian sarcoma | Monkey | | One chain of PDGF |
| src | Rous sarcoma | Chicken | | TyrPK |
| ski | SKV770 | Chicken | | Nuclear |
| trk | NVT | Human | Colon carcinoma | TyrPK GFR L |
| yes | Y73, Esh sarcoma | Chicken | | TyrPK(src) |

Suitable viral vector constructs are those known in the art. For example, vectors derived from a parvovirus (U.S. Pat. Nos. 5,252,479 and 5,624,820), a paramyxovirus such as simian virus 5 (SV5) (U.S. Pat. No. 5,962,274), a retrovirus such as HIV (U.S. Pat. Nos. 5,753,499 and 5,888,767), and a baculovirus such as a nuclear polyhedrosis virus (U.S. Pat. No. 5,674,747) can be used. Vectors derived from adenovirus have been extensively studied (U.S. Pat. Nos. 5,670,488, 5,817,492, 5,820,868, 5,856,152 and 5,981,225 all incorporated herein by reference).

The nucleic acid molecule can be delivered directly to a tissue of the host animal by injection, by gene gun technology or by lipid mediated delivery technology. The injection can be conducted via a needle or other injection devices. The gene gun technology is disclosed in U.S. Pat. No. 5,302,509 and the lipid mediated delivery technology is disclosed in U.S. Pat. No. 5,703,055.

In still another specific embodiment, the nucleic acid molecule is delivered to a cell of host animal ex vivo and the cell is then delivered to a suitable tissue of the host animal, preferably through injection or intravenous drip.

General methods for ex vivo transduction and whole animal administration include $Ca_3(PO_4)_2$-DNA transfection (Sambrook, et al., *Molecular Cloning*, 2nd Edition, Plainview, N.Y. Cold Spring Harbor Press, 1989), DEAE dextran-DNA transfection (Sambrook, et al., *Molecular Cloning*, 2nd Edition, Plainview, N.Y. Cold Spring Harbor Press, 1989), electroporation (e.g., protocols from Bio-Rad), transfection using "LIPOFECTIN"™ reagent (e.g., protocols from BRL-Life Science), gene gun technology (U.S. Pat. No. 5,302,509), or viral gene delivery system (Kaplitt, et al., Viral Vectors, Academic Press, Inc., 1995).

Although the prodrug and the selenium prodrug lyase may be delivered concomitantly, it is preferred that the enzyme be provided first, followed by administration of the selenium-containing prodrug. This is in order that the cells will be preconditioned to generate the toxic form of selenium. In any event, the tumor to be treated must be proximal both to the lyase and the prodrug to elicit the toxic response.

In addition to the selenium-containing prodrug and the prodrug lyase, chemotherapeutic agents can be employed in suitable therapeutic protocols. Such agents as 5-FU, cyclophosphamide, doxorubicin, BCNU, methotrexate and other drugs may be employed along with the protocols of the invention. The efficacy of these drugs is enhanced by the lyase and the prodrug.

The tumors to be treated may include solid tumors such as those of the breast, prostate, colon, lung, brain, pancreas, liver, and the like or may be lymphomas or other leukemias or metastases of solid tumors. The selection of the appropriate expression system both from the standpoint of the vector and the control sequences for expression will depend on the nature of the tumor targeted. The nucleotide sequence encoding the enzyme may also be provided with a fusion amino acid sequence which confers target specificity, as was the case for direct administration of the enzyme.

The following examples are intended to illustrate but not to limit the invention.

EXAMPLE 1

Construction of a Methioninase-Producing Vector

FIG. 1 shows a diagram of a vector constructed to provide viral infection of tumor cells and expression the methioninase derived from *P. putida*. The nucleotide sequence encoding the enzyme is placed under control of the CMV-5 promoter and enhancer. The backbone vector is commercially available. The resulting vector is propagated according to standard techniques in adenovirus.

To prepare the vector, the methioninase gene cloned from *P. putida* as described in Inoue, H.,et al, *J. Biochem* (1995) 117:1120–1125 was amplified by PCR and the 1.2 kb gene was ligated into the transfer vector pQBI-Ad CMV 5GFP (obtained from Quantum, Montreal, Quebec, Canada) downstream of the CMV-5 promoter at the BglII/PmeI site. The resulting vector is shown in FIG. 1. The vector was cotransfected into 293A cells (Quantum) using the calcium phosphate method along with Ad CMV Lac ZΔE1/Δ3 viral DNA cut with ClaI (Quantum). Transfected cells were overlain with 1.25% Sea Plaque agarose (FMC Bioproducts, Rockland, Me) and incubated at 37° C. for 14–21 days. Primary plaques were isolated and used to infect 293A cells to generate primary crude viral lysate. Methioninase gene expression in the viral lysate was confirmed by an enzymatic assay. After a second plaque purification, a single plaque was amplified in 293A cells. Ad CMV 5GFP ΔE1/ΔE3 was used as a control vector (-rAd) and purchased from Quantum. The control rAd was expanded in 293A cells and purified by cesium chloride centrifugation and subsequent fractionation on Sephadex G25. The above-described construction of rAd-MET is reported by Miki, K., et al., Cancer Res. (in press) incorporated herein by reference.

EXAMPLE 2

Effect of Varying Methioninase in the Presence of Selenomethionine on Various Tumor Cell Lines Cells ($4 \times 10^3$) of various tumor lines were seeded onto 96-well plates. After 24 hours, serial dilutions of the methioninase expressing vector (rAd-MET) or a control vector containing no methioninase encoding nucleotide sequence (rAd) were added to the wells with and without 20 μM of selenomethionine (SeMet) (20 μM). After incubating the plates for three (3) days, the medium was replaced with 0.5 mg/ml MTT for two (2) hours and analyzed using a microplate reader (BioRad), in a standard MTT assay. Results were recorded as percentage of surviving cells.

Figure 2:
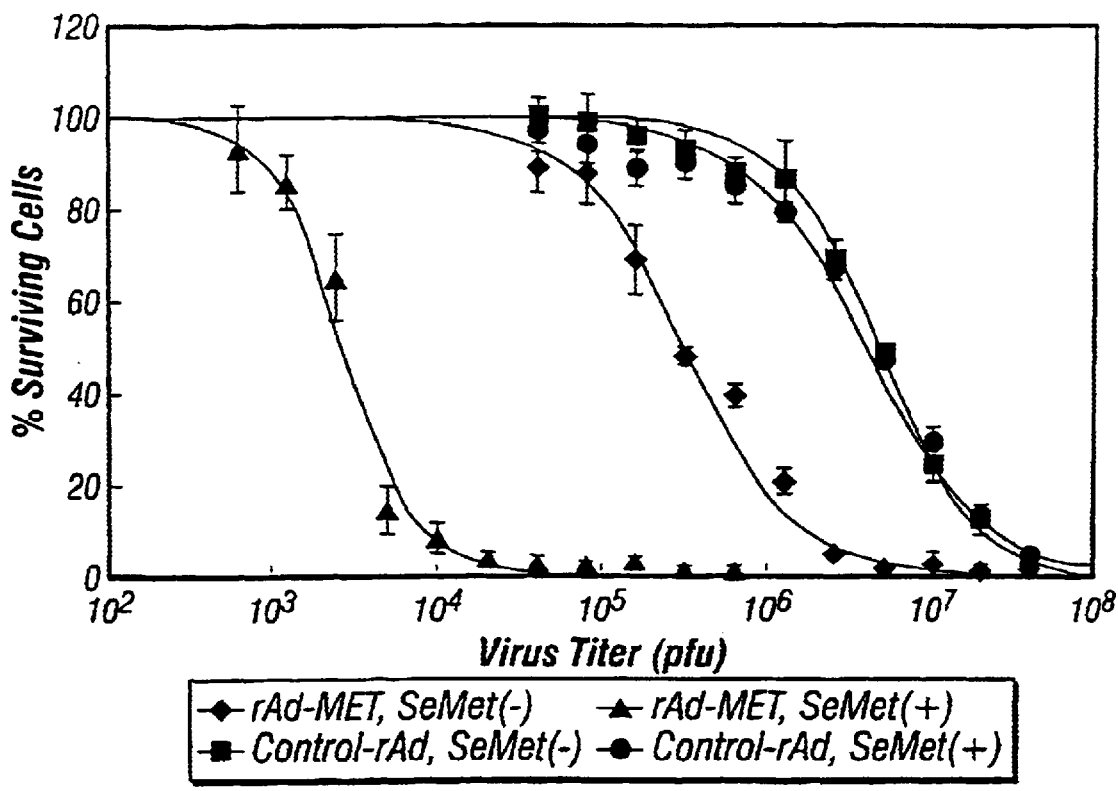
FIG. 2 shows the effect of various virus titers of the methioninase-providing virus on cell survival in the presence and absence of SeMet using OVCAR-8 cells.
Figure 3:
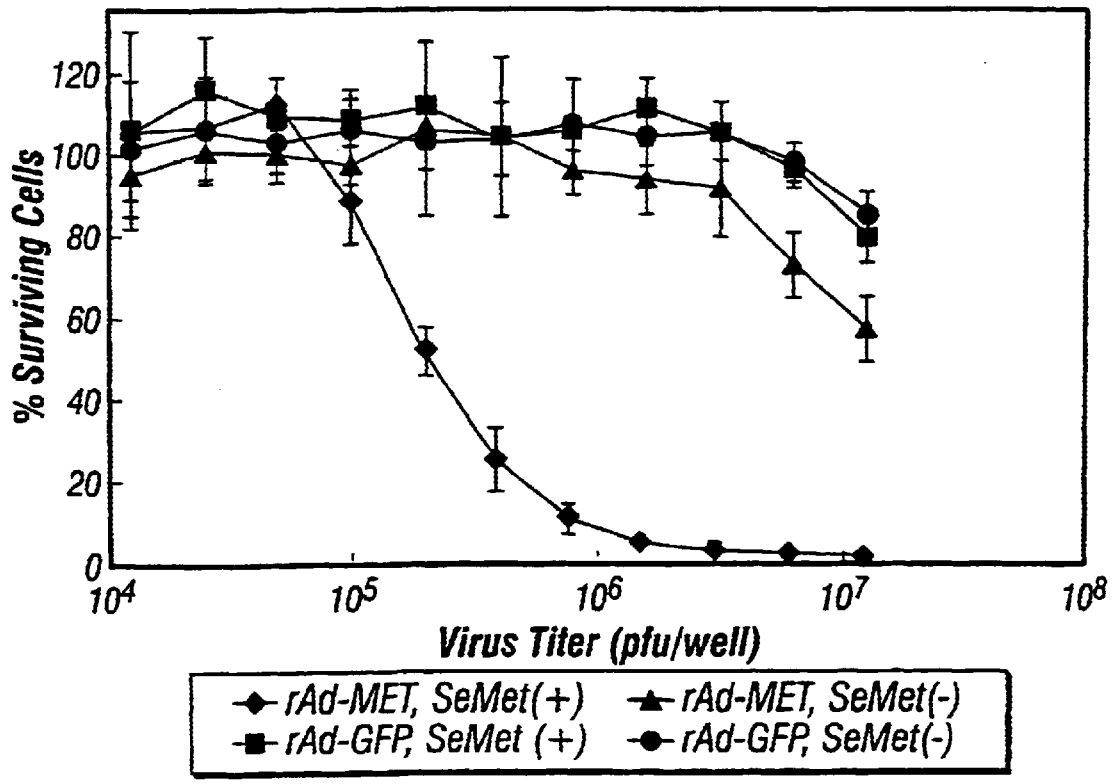
FIG. 3 shows the effect of various virus titers of the methioninase-providing virus on cell survival in the presence and absence of SeMet using A204 cells.
Figure 4:
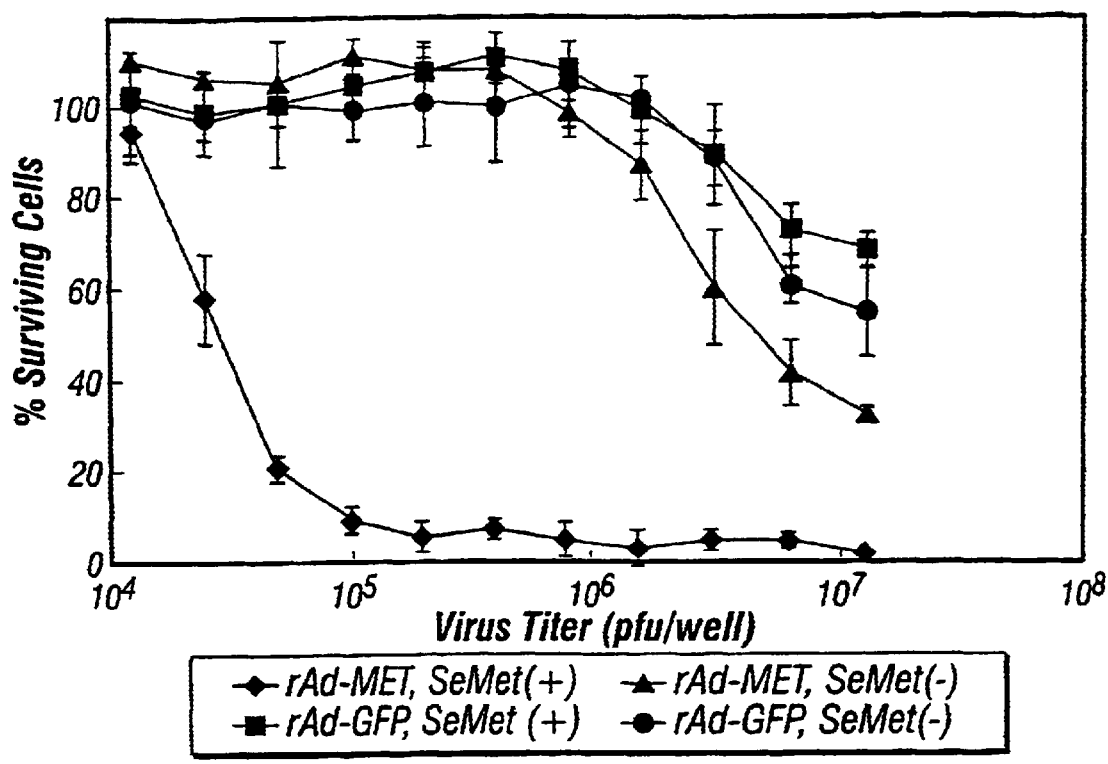
FIG. 4 shows the effect of various virus titers of the methioninase-providing virus on cell survival in the presence and absence of SeMet using PC-3 cells.
Figure 5:
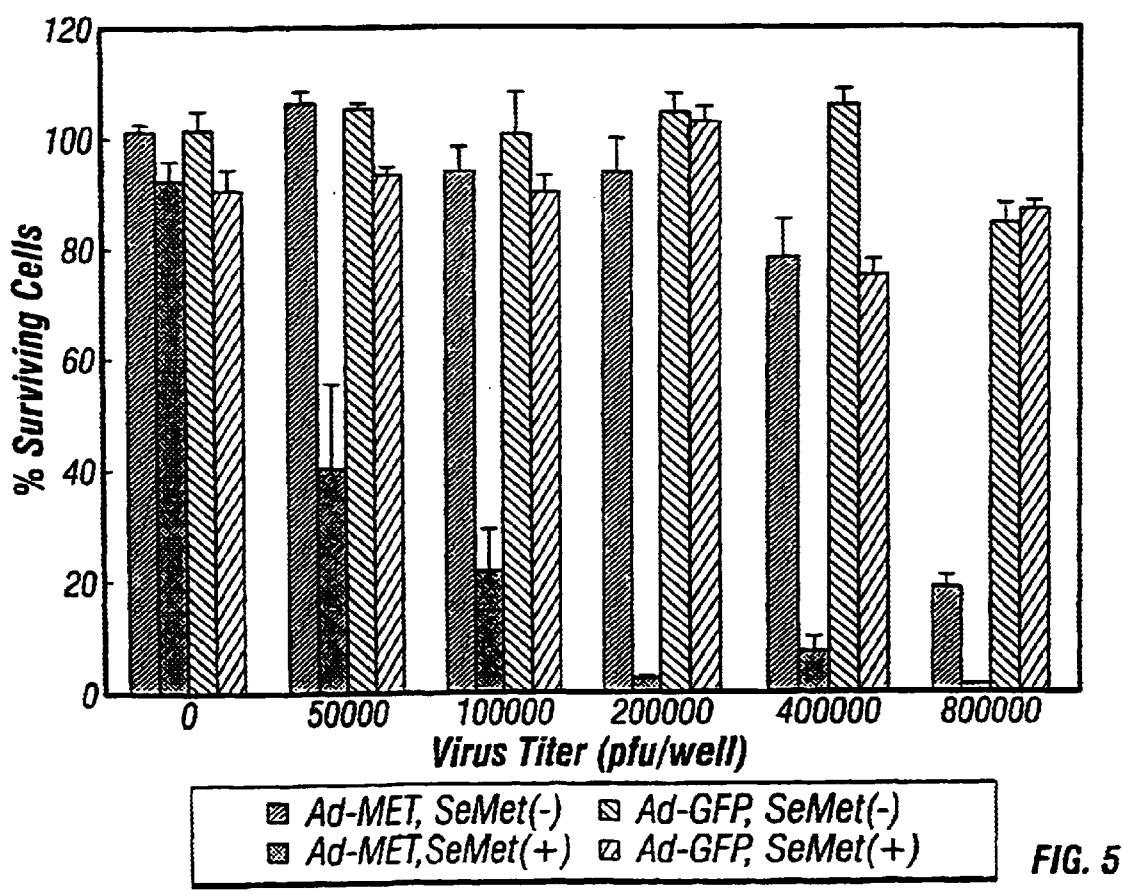
FIG. 5 shows the effect of various virus titers of the methioninase-providing virus on cell survival in the presence and absence of SeMet using A549 cells.

The cell lines tested were human cancer cell lines OVCAR-8 (ovarian cancer), A549 and EKVX (lung cancer), Hep-2 (head and neck cancer), MIA PaCa-2 and BxPC-3 (pancreatic cancer), human rhabdomyosarcoma cell line A204 and human prostate cell line PC-3. The results with respect to the OVCAR-8 cell line and cell lines A204, and PC-3 are shown in FIGS. 2, 3 and 4 in X/Y graphs; FIG. 5 is a bar graph of the results with respect to the A549 cell line. In each case, the presence of SeMet drastically lowered the $IC_{50}$ for the rAd-MET vector. The results are further summarized in Table 1.

TABLE 1

Comparison of $IC_{50}$ of rAd-MET and Control-rAd in human tumor cell lines with or without SeMet

| | $IC_{50}$ rAd-MET (pfu) | | $IC_{50}$ Control-rAd (pfu) | |
| --- | --- | --- | --- | --- |
| cell lines | SeMet (+) | SeMet (−) | SeMet (+) | SeMet (−) |
| OVCAR-8 | $2.7 \times 10^3$ | $3.0 \times 10^5$ | $3.8 \times 10^6$ | $4.6 \times 10^6$ |
| A549 | $7.0 \times 10^3$ | $3.3 \times 10^5$ | $6.7 \times 10^5$ | $8.0 \times 10^5$ |
| Hep-2 | $5.9 \times 10^3$ | $3.3 \times 10^5$ | $7.9 \times 10^5$ | $5.9 \times 10^5$ |
| MIA PaCa-2 | $1.7 \times 10^4$ | $3.6 \times 10^5$ | $9.3 \times 10^5$ | $1.1 \times 10^6$ |

TABLE 1-continued

Comparison of $IC_{50}$ of rAd-MET and Control-rAd in human tumor cell lines with or without SeMet

| | $IC_{50}$ rAd-MET (pfu) | | $IC_{50}$ Control-rAd (pfu) | |
|---|---|---|---|---|
| cell lines | SeMet (+) | SeMet (−) | SeMet (+) | SeMet (−) |
| BxPC-3 | $3.5 \times 10^4$ | $3.1 \times 10^6$ | $2.7 \times 10^6$ | $3.0 \times 10^6$ |
| EKVX | $3.7 \times 10^3$ | $4.8 \times 10^5$ | $1.2 \times 10^6$ | $1.7 \times 10^6$ |

As seen from the table, the $IC_{50}$ values in the presence, as compared to the absence, of SeMet are approximately two orders of magnitude less for all cell lines. rAd-MET, as expected, even in the absence of SeMet has some effect.

EXAMPLE 3

Effect of Varying SeMet in the Presence of Methioninase

Figure 6:
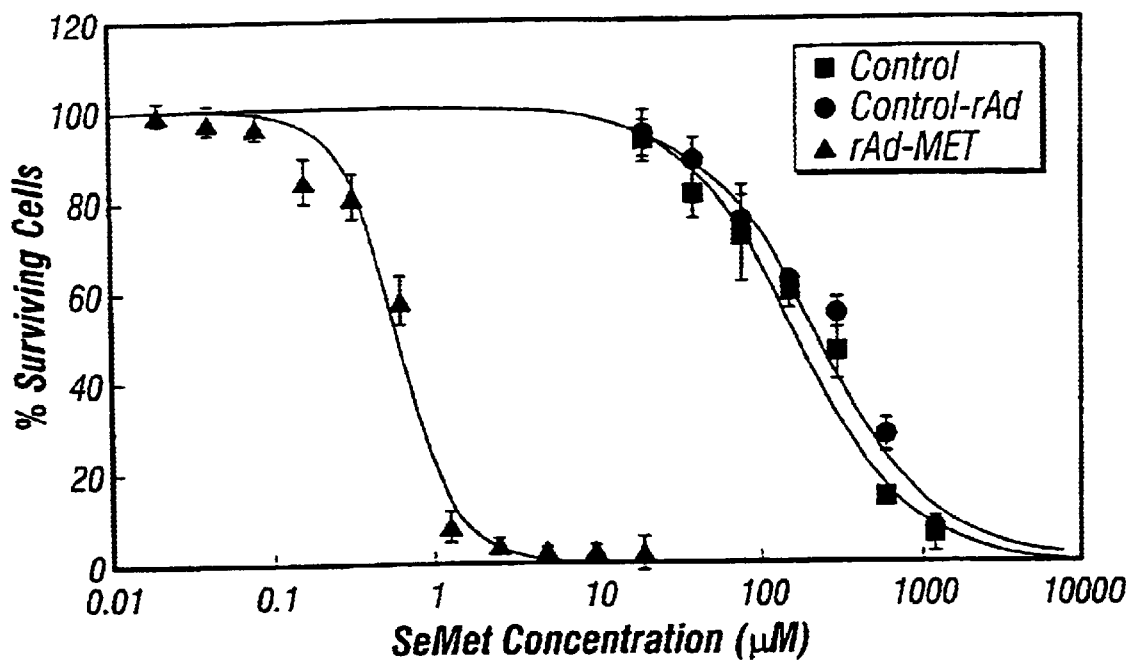
FIG. 6 shows the effect of SeMet concentration on OVCAR-8 cells transduced with rAd-MET.

The cell lines were also evaluated for their response to varying concentrations of SeMet. In these protocols, the cells were seeded as above into 96-well plates and infected with $4 \times 10^5$ pfu of rAd-MET or control rAd. After 24 hours, serial dilutions of SeMet were added and three (3) days later cytotoxicity was evaluated with the MTT assay as described in Example 2. The results are shown for OVCAR-8 cells in FIG. 6. As seen, the $IC_{50}$ for SeMet is lowered over a thousandfold in the presence of rAd-MET as compared to control rAd. A summary of the $IC_{50}$ values for a number of cell lines is shown in Table 2.

TABLE 2

Comparison of SeMet $IC_{50}$ in human tumor cell lines transdued with rAd-MET

| | | SeMet $IC_{50}$ ($\mu M$) | |
|---|---|---|---|
| cell lines | rAd-MET | Control-rAd | Wild Type |
| OVCAR-8 | 0.59 | 170.3 | 223.6 |
| A549 | 0.5 | 327.1 | 485.9 |
| Hep-2 | 1.66 | 387 | 411 |
| MIA PaCa-2 | 3.86 | 338 | 422 |
| BxPC-3 | 3.38 | 222.6 | 311.8 |
| EKVX | 1.66 | 686.4 | 1360 |

Virtually all cell lines showed a dramatic decrease in $IC_{50}$ for SeMet in the presence of rAd-MET.

EXAMPLE 4

Combined Variation of rAd-MET and SeMet on A549 Cells

The experiments described in Examples 2 and 3 were performed on A549 human lung cancer cells using varying concentrations of SeMet from 0–40 $\mu M$ and of virus rAd-MET titer of $0-8 \times 10^5$ pfu using rAd as a control. Percentage of surviving cells was again used as an index of efficacy.

Figure 7:
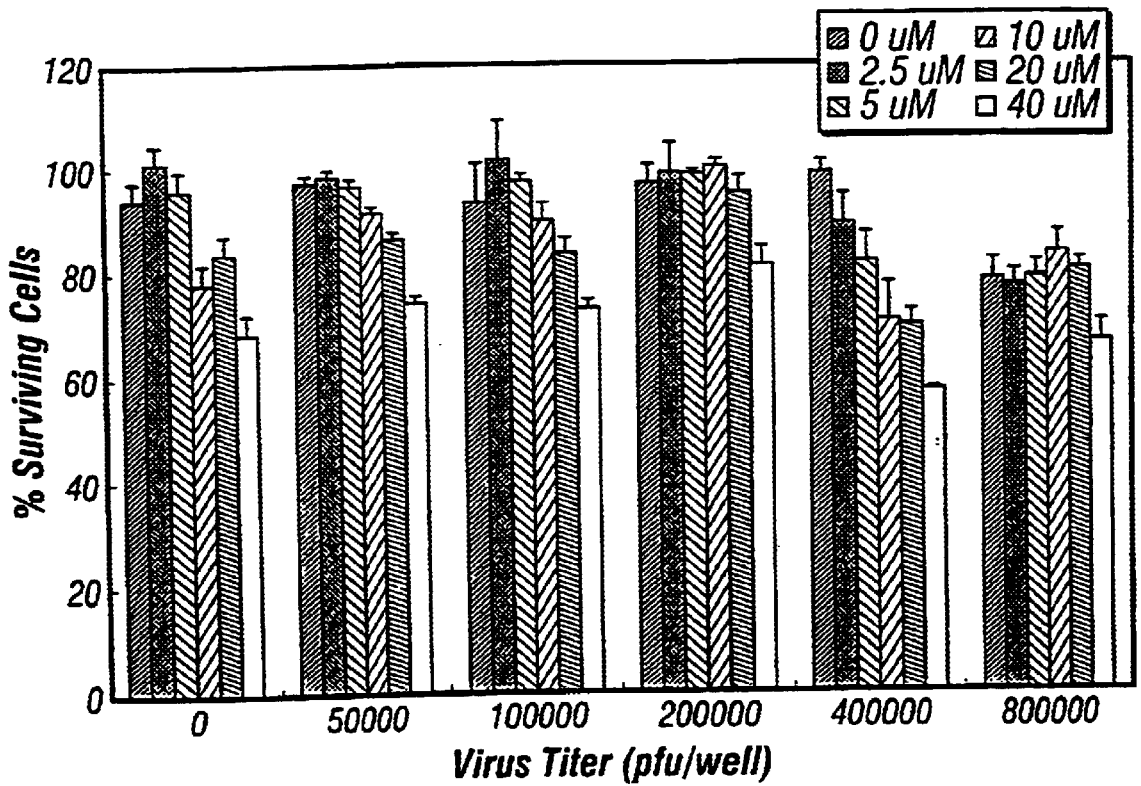
FIG. 7 shows the combined effect of various concentrations of SeMet and various titers of control rAd on cell survival for A549 cells.

As shown in FIG. 7, when the control vector was employed, the virus titer was substantially irrelevant to the results. Selenomethionine itself showed slight toxicity at 20–40 $\mu M$.

Figure 8:
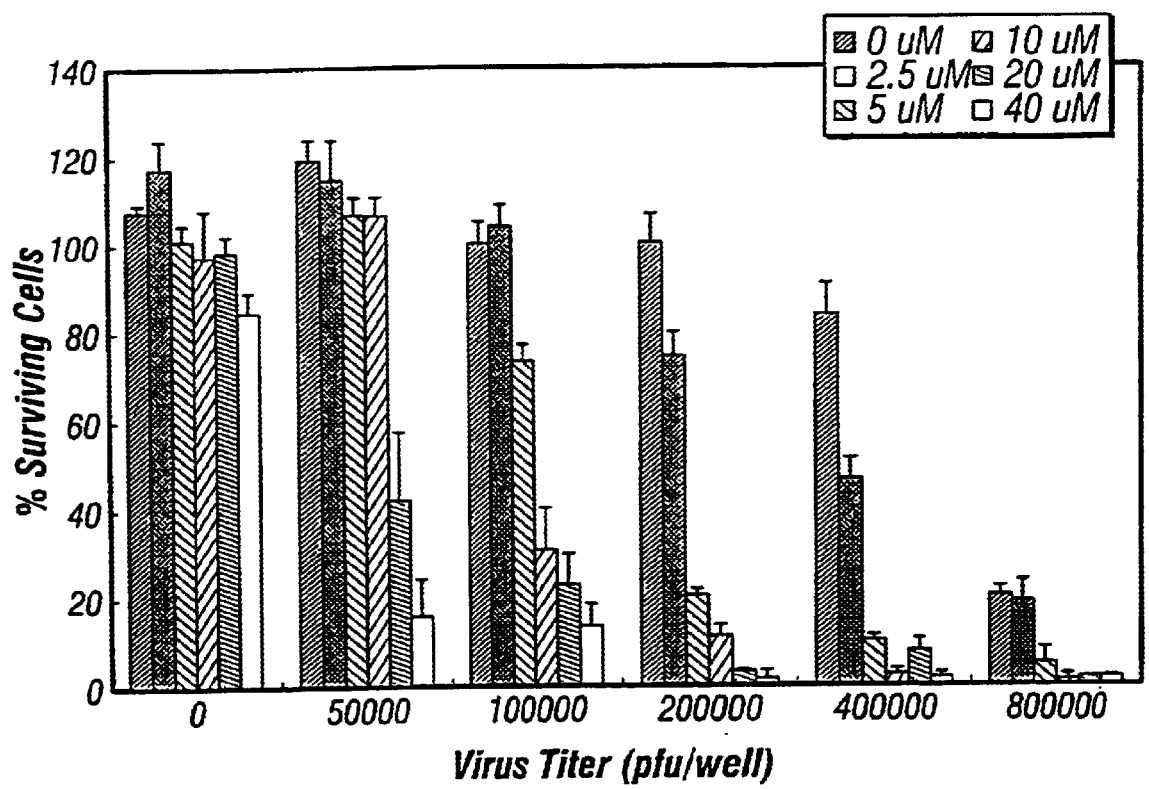
FIG. 8 shows the combined effect of concentration of SeMet and virus titers for rAd-MET on survival of A549 cells.

However, as shown in FIG. 8, when rAd-MET was provided, even at virus titers of 5,000 pfu, 20–40 $\mu M$ of SeMet drastically reduced viability. At virus titers of $4 \times 10^5$, even 2.5 $\mu M$ SeMet provided toxicity such that only 50% of the cells survived. At $8 \times 10^5$ pfu, the vector alone was sufficient to be cytotoxic, but concentrations of SeMet of 5 $\mu M$ or more, substantially no cells survived.

EXAMPLE 5

Bystander Effect

Figure 9:
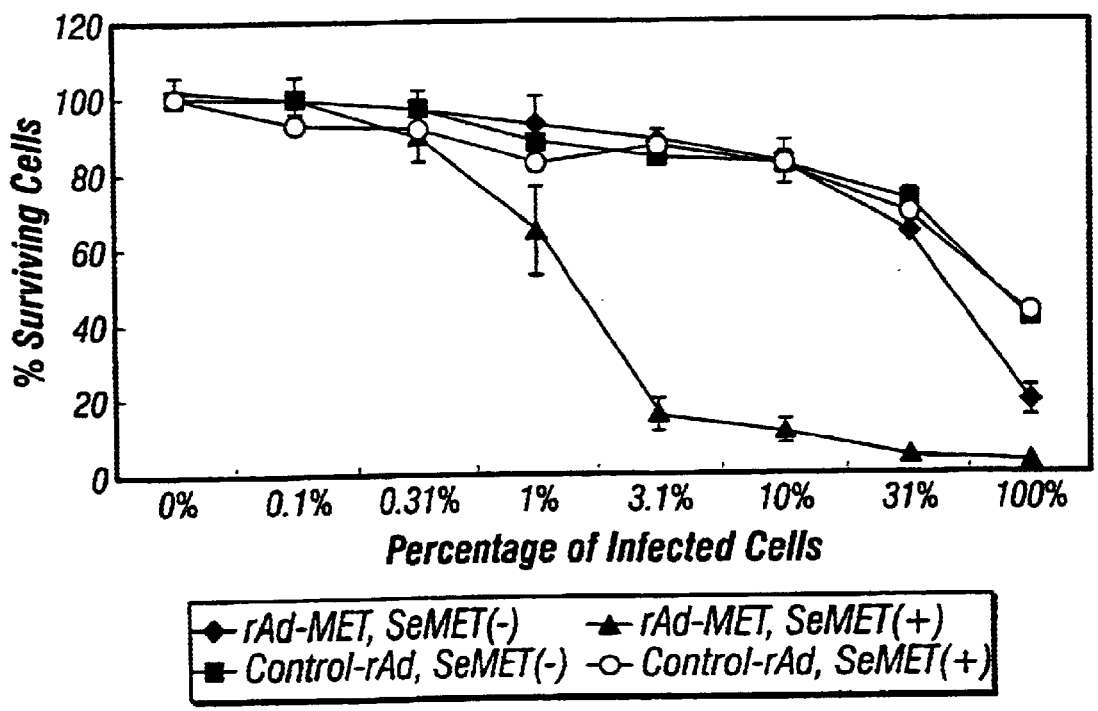
FIG. 9 shows the bystander effect of rAd-MET and SeMet in combination on A549 cells.

A549 human lung cancer cells transduced with rAd-MET or control rAd (MOI 50) were mixed with non-transduced cells at various ratios in the presence of 20 $\mu M$ SeMet. Cytotoxicity was analyzed with the MTT assay described above after three (3) days. FIG. 9 shows the results as a function of the percentage of infected cells.

As shown, cells transduced with rAd either in the absence of SeMet or in the presence of SeMet, and cells transduced with rAd-MET in the absence of SeMet exhibited no ability to kill bystander cells. On the other hand, cells that had been transduced with rAd-MET were able to destroy bystander cells in the presence of SeMet significantly even when they were present in the culture at a proportion as low as 1%. When present at 3.1% of the culture, these cells killed 80% of the non-transduced cells.

EXAMPLE 6

Confirmation of Apoptosis

Figure 10A:
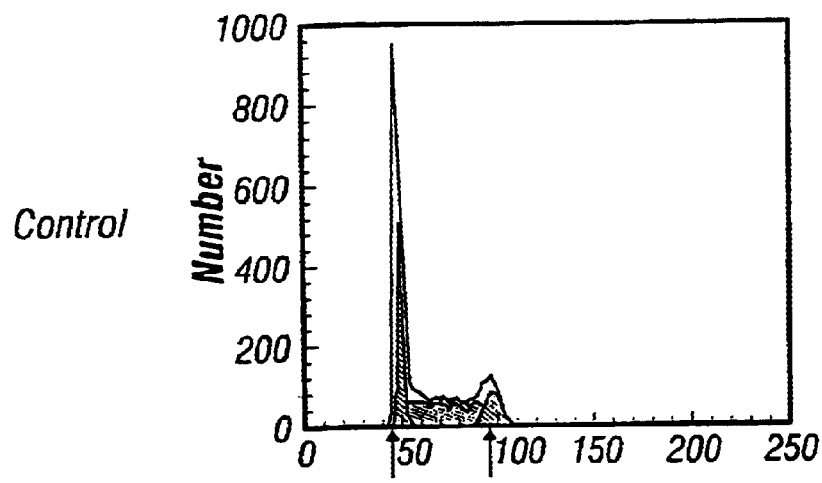
FIG. 10 shows the induction of apoptosis by the combination of rAd-MET and SeMet on A549 cells.
Figure 10B:
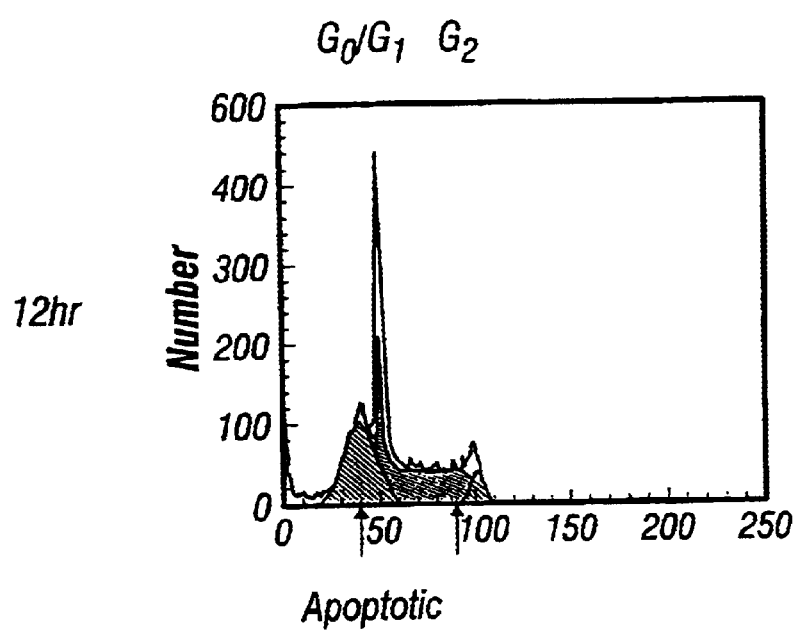
Figure 10C:
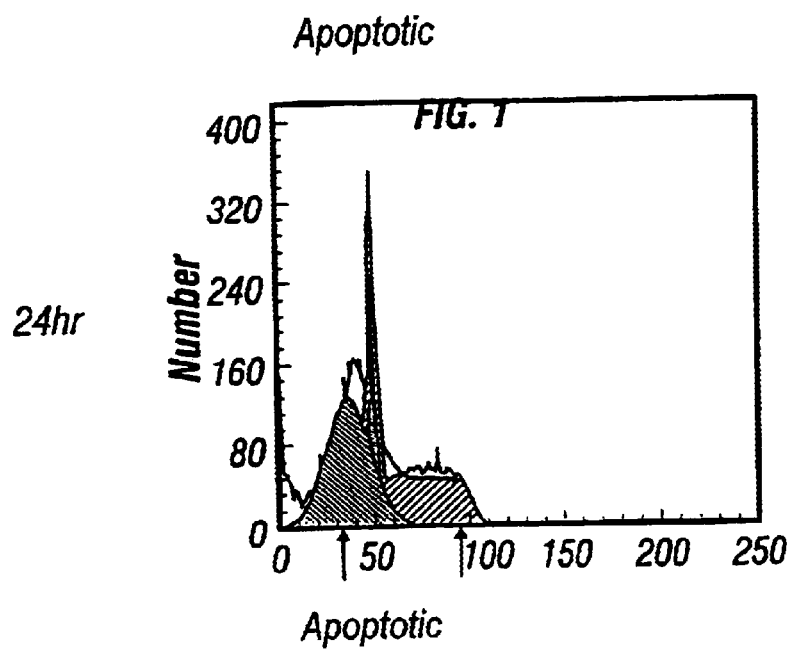

A549 cells ($1 \times 10^6$) were transduced with rAd-MET (MOI 20). After 24 hours, 20 $\mu M$ SeMet was added. At various times, the cells were harvested and fixed with 70% ethanol and stained with 50$\mu g$/ml propidium iodide. The DNA content of the stained cells was evaluated by FACS. As shown in FIG. 10, after 12 hours of exposure to SeMet, an increase in fluorescence labeling in the $G_0$ population was observed indicating the presence of apoptotic cells. The proportion-of these cells increased after 24 hours exposure to SeMet. The apoptotic effect was confirmed by electrophoresing the extracted DNA after 6, 12 and 24 hours. The electrophoresis results showed nucleosomal DNA fragmentation, confirming this result. It was also confirmed by showing cytochrome C release into the cytosol of cells infected with rAd-MET but not of cells infected with rAd.

EXAMPLE 7

ROS Generation

It is believed that selenium cytotoxicity is mediated by generation of reactive oxygen species (ROS). This can be measured by standard techniques which employ lucigenin-dependent chemiluminescence as described by Yan, L., et al., *Biochem Pharmacol* (1993) 45:429–437, cited above.

A549 cells were transduced with rAd-MET at MOI of 50, 24 hours before measurement. The cells ($1 \times 10^6$) were incubated in 1 ml RPMI in the presence of SeMet with or without 10 units of superoxide dismutase (SOD) for 30 minutes. Lucigenin (50 $\mu g$) was added to the cell suspension just prior to measurement and integrated chemiluminescence was measured for 10 seconds, three times, using a TD21 luminometer (Turner Designs).

Figure 11:
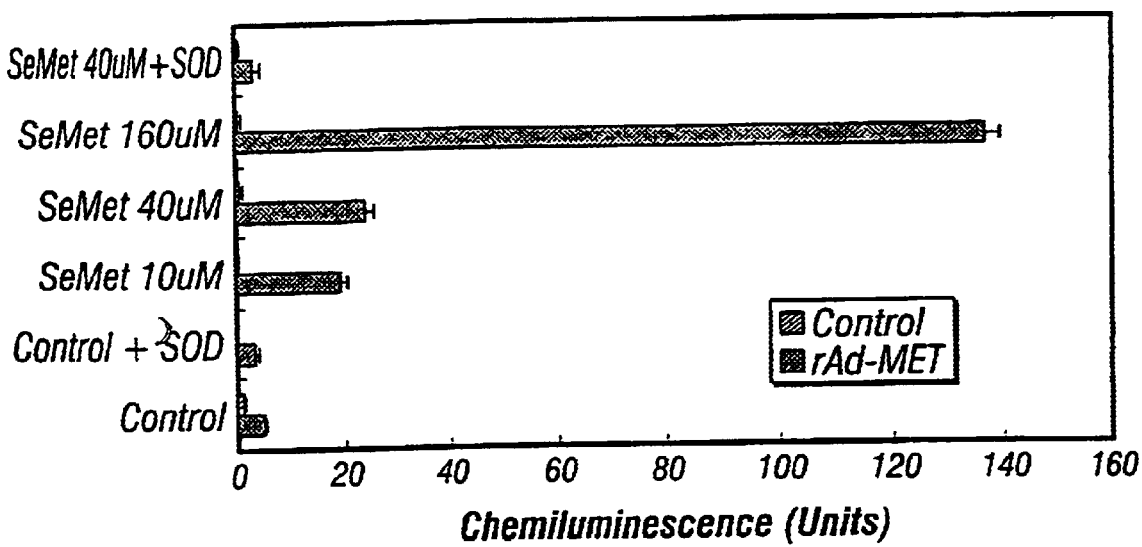
FIG. 11 shows the generation of oxidant by rAd-MET in combination with SeMet as detected by chemiluminescence of lucigenin.

Chemiluminescence levels were dependent on SeMet concentration and were inhibited by SOD. As shown in FIG. 11, chemiluminescence in the presence of 160 $\mu M$ SeMet was-over 100 times that of the control and was inhibited by SOD. At 40 $\mu M$, it was 20 times control and inhibited by SOD.

The high level of oxidation was also confirmed by measuring GSH content. Cells ($2 \times 10^6$) were infected with rAd- MET or control rAd at MOI of 20, 24 hours before treating with 20 μM SeMet. The cells were then lysed and then incubated with 0.05% o-phthalaldehyde for 15 minutes and the GSH content was measured fluorometrically using 350 nM excitation and 420 nM emission. The glutathione content in cells transduced with control rAd remained substantially constant over 24 hours while the cells transduced with rAd-MET showed a reduction in GSH level from about 110 mg GSH/mg protein at time 0 to 80 mg/mg after 6 hours, 60 mg/mg after 12 hours and to less than 10 mg/mg after 24 hours.

EXAMPLE 8

Mitochondrial Permeability

In further confirmation that the selenol poisoning is mediated by oxidation, advantage was taken of the known phenomenon whereby oxidants cause mitochondrial swelling and loss of membrane potential (see, Green, D.R., et al., *Science* (1998) 281:1309–1312; Cai, J., et al., *Biochem Biophys Octa*, (1998) 1366:139–149). It was confirmed that when cells were infected with rAd-MET (MOI 50) and later treated with 20 μM SeMet, after 24 hours incubation, the mitochondrial membranes were disrupted. Mitochondrial membrane potential changes were monitored with the fluorescence dye Mitosensor™ which is normally taken up in the mitochondria where it forms aggregates that exhibit intense red fluorescence. In cells treated as described, Mitosensor™ does not accumulate in the mitochondria and remains in the cytoplasm where it fluoresces green.

Figures 12A, 12B, 12C:
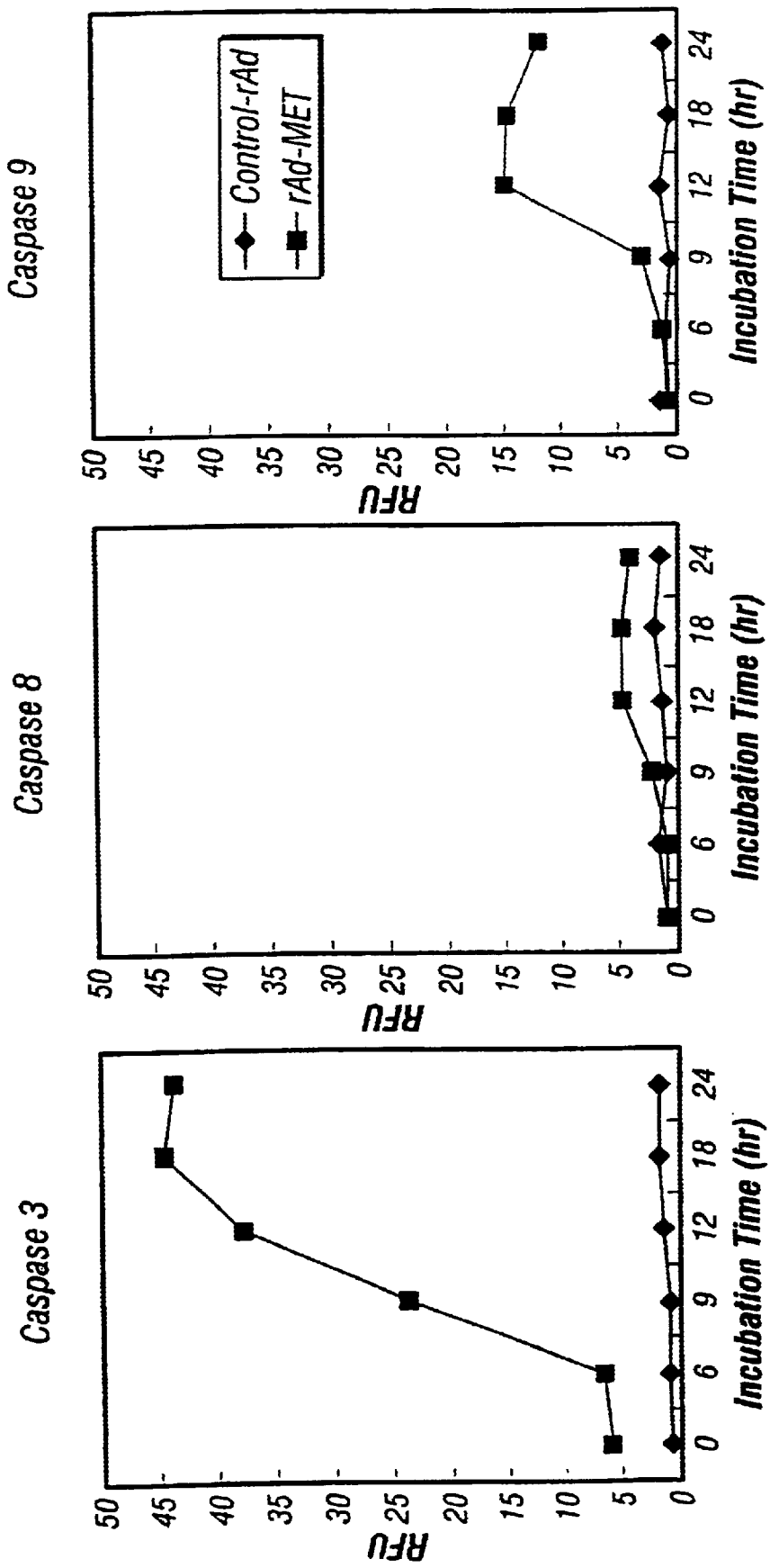
FIG. 12 shows the effect of the combination of SeMet and rAd-MET on caspase concentrations in lysates of A549 cells.

In an additional experiment, cells were treated as above except that an MOI of 20 was used. And the levels of caspase 3, caspase 8 and caspase 9 were measured at varying times. As shown in FIG. 12, caspase 8 remained relatively constant but caspase 3 and caspase 9 in the lysates increased with time in the treated cells.

Further, mitochondrial swelling in the cells treated as described was visualized by eletron microscopy; after 24 hours, most mitochondria were quite swollen.

EXAMPLE 9

In Vivo Treatment

Figure 13:
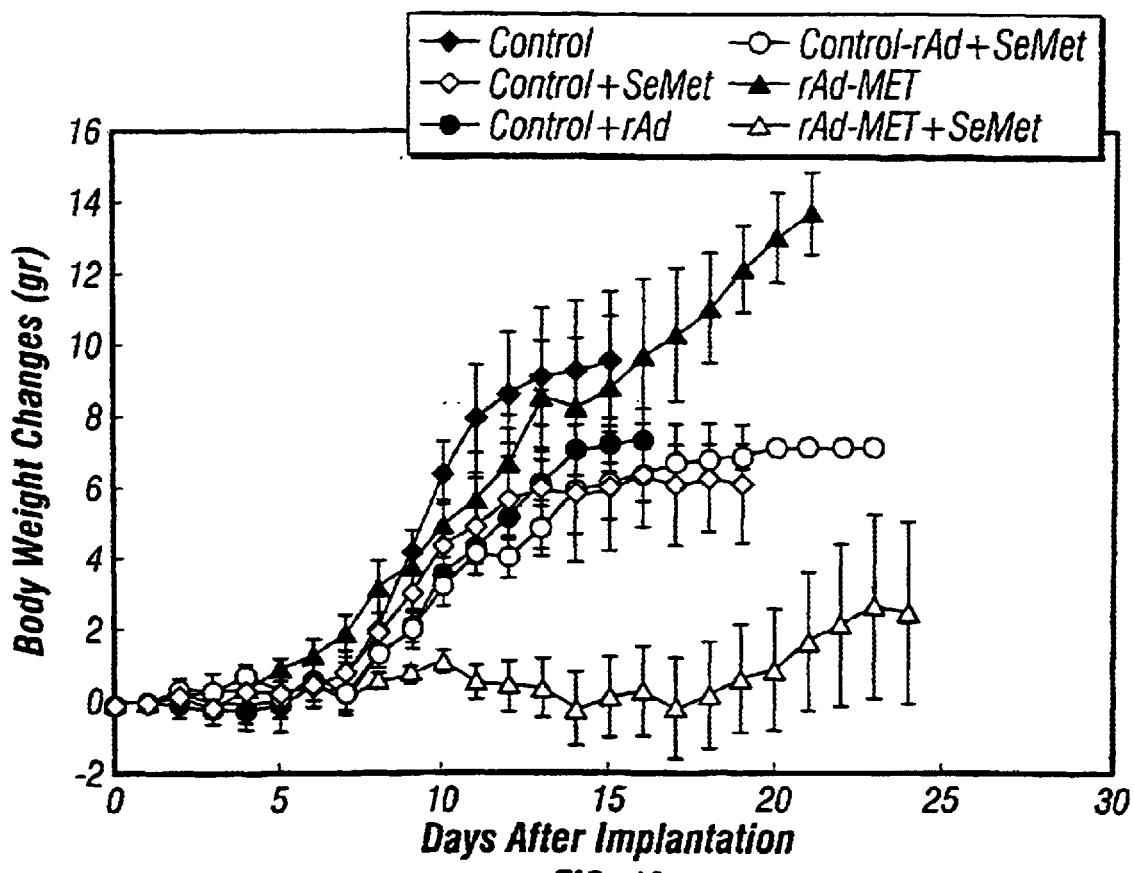
FIG. 13 shows the effect of the combination of rAd-MET and SeMet on ascites tumor growth in vivo.
Figure 14:
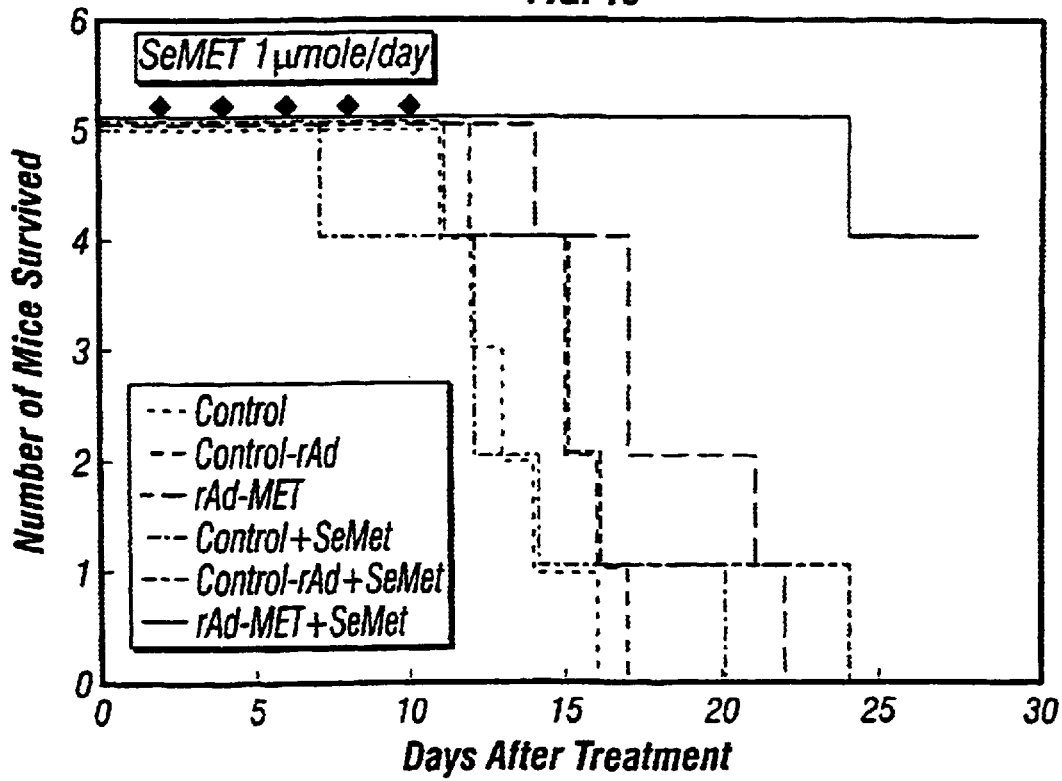
FIG. 14 shows the effect of the combination of rAd-MET and SeMet on survival of nude mice containing ascites tumors.

N1S1 rat hepatoma tumor cells (1×106 cells) were implanted into peritoneal cavities of female nude mice. Two days after implantation, either control rAd or rAd-MET (5×10$^8$ pfu) or mock control were injected every other day for a total of five (5) injections. The mice were also treated IP with either 1 μM SeMet or normal saline daily from day 3 to day 13. Ascites tumor growth was evaluated by body weight gain. FIG. 13 shows the results over 25 days. As shown, even over this period, the mice treated with rAd-MET and SeMet failed to gain significant amounts of weight. This was confirmed by observation, and, in FIG. 14, by the number of mice surviving as shown.

EXAMPLE 10

Combined Effect of SeMet With Chemotherapeutic Agents

A549 cells that had been transfected with rAd-MET were cultured in RPMI with 20% FBS with and without 8 μM SeMet. In each case, duplicate samples were cultured without BCNU and in the presence of 300 μM BCNU. Cell survival was determined after hours. With no treatment, 100% of the cells survived; in the presence of SeMet alone, 80% of the cells survived. In the absence of SeMet, but in the presence of BCNU, 55% cell survival was obtained; in the presence of 8 μM SeMet and 300 μM BCNU, less than 10% of the cells survived. Thus, SeMet dramatically enhances the effect of BCNU.

In a similar experiment, A549 cells that had been transfected with rAd-MET were cultured in RPMI with 10% FBS in the presence and absence of 4 μM SeMet and with and without 0.4 μM doxorubicin. In the presence of doxorubicin alone, a 75% cell survival rate was obtained; when SeMet was present alone, a 60% cell survival rate was obtained. However, a combination of these compounds resulted in cell survival of only 10%.

What is claimed is:

1. A method to inhibit the growth of tumor cells in a subject in vivo which method comprises
    a) administering to a subject in need of such inhibition a selenium-containing prodrug and
    b) administering directly to a tumor contained in said subject a methionine γ-lyase protein;
    whereby said lyase releases at said tumor a toxic form of selenium from said prodrug, in an amount sufficient to inhibit tumor cell growth.

2. The method of claim 1 wherein said prodrug is selenomethionine.

3. The method of claim 1 which her comprises administering a chemotherapeutic agent to said subject.

4. The method of claim 3 wherein said agent is BCNU.

5. The method of claim 1 wherein step b) is performed prior to step a).

6. The method of claim 1 wherein steps a) and b) are preformed concomitantly.

* * * * *